(12) United States Patent
Ng

(10) Patent No.: US 7,303,527 B2
(45) Date of Patent: Dec. 4, 2007

(54) MEDICAL EXAMINATION APPARATUS

(76) Inventor: Raymond C. Ng, Room 803, Manning House, 48 Queen's Road, Central (HK)

( * ) Notice: Subject to any disclaimer, the term of this patent is extended or adjusted under 35 U.S.C. 154(b) by 491 days.

(21) Appl. No.: 10/898,908

(22) Filed: Jul. 26, 2004

(65) Prior Publication Data

US 2006/0020163 A1    Jan. 26, 2006

(51) Int. Cl.
*A61B 1/00*    (2006.01)
(52) U.S. Cl. ............... 600/102; 248/124.1; 248/125.8; 248/176.3
(58) Field of Classification Search ............... 600/102; 606/130; 248/124.1, 125.7, 125.8, 125.9, 248/176.1, 176.3, 274.1, 276.1, 278.1
See application file for complete search history.

(56) References Cited

U.S. PATENT DOCUMENTS

| | | | |
|---|---|---|---|
| 947,153 A | 1/1910 | Forth | |
| 3,185,422 A | 5/1965 | Spindler | |
| 3,971,538 A | 7/1976 | Marvich | |
| 4,170,336 A | 10/1979 | Malis | |
| 4,617,915 A * | 10/1986 | Arakawa | 600/131 |
| 4,744,536 A * | 5/1988 | Bancalari | 248/125.8 |
| 5,228,429 A * | 7/1993 | Hatano | 600/102 |
| 5,470,037 A | 11/1995 | Willis | |
| 5,571,072 A | 11/1996 | Kronner | |
| 5,873,815 A * | 2/1999 | Kerin et al. | 600/114 |
| 5,907,664 A * | 5/1999 | Wang et al. | 700/251 |
| 5,951,461 A * | 9/1999 | Nyo et al. | 600/118 |
| 6,024,695 A * | 2/2000 | Taylor et al. | 600/102 |
| 6,120,433 A * | 9/2000 | Mizuno et al. | 600/102 |
| 6,514,239 B2 * | 2/2003 | Shimmura et al. | 606/1 |
| 6,569,084 B1 * | 5/2003 | Mizuno et al. | 600/102 |
| 6,592,086 B1 | 7/2003 | Sander | |
| 2003/0191455 A1* | 10/2003 | Sanchez et al. | 606/1 |
| 2004/0138524 A1* | 7/2004 | Ueda et al. | 600/102 |
| 2004/0210106 A1* | 10/2004 | Banju | 600/102 |
| 2005/0085689 A1* | 4/2005 | Pagliuca et al. | 600/102 |

* cited by examiner

*Primary Examiner*—John P. Leubecker
(74) *Attorney, Agent, or Firm*—William W. Haefliger

(57) ABSTRACT

Apparatus for effecting or controlling instrumentation insertible into the human body, as for example into the uterus, comprising in combination a first suspension for adjustably suspending the instrumentation generally vertically; a second suspension operatively connected with the first suspension for adjustably suspending the instrumentation for generally horizontal movement; a third suspension for adjustably suspending the first and second suspensions for generally vertical movement to selected level of the instrumentation; and a swivel connection allowing swiveling of the instrumentation about a generally vertical axis.

16 Claims, 3 Drawing Sheets

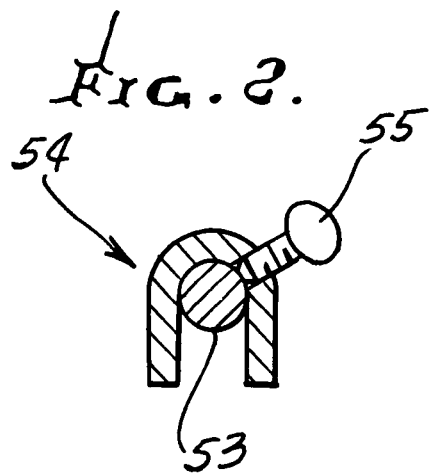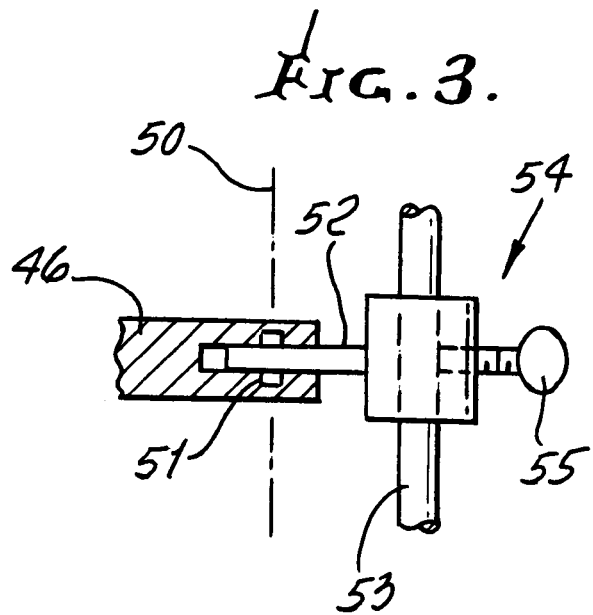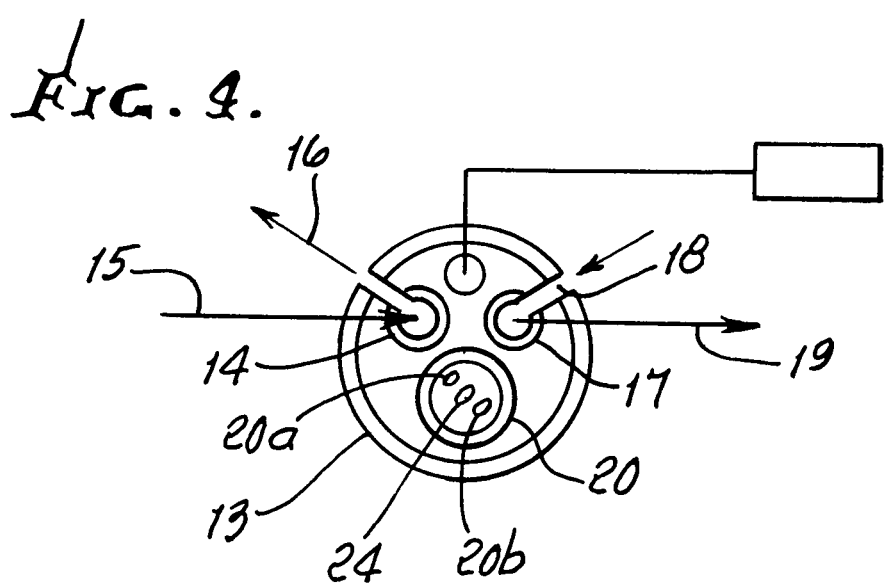

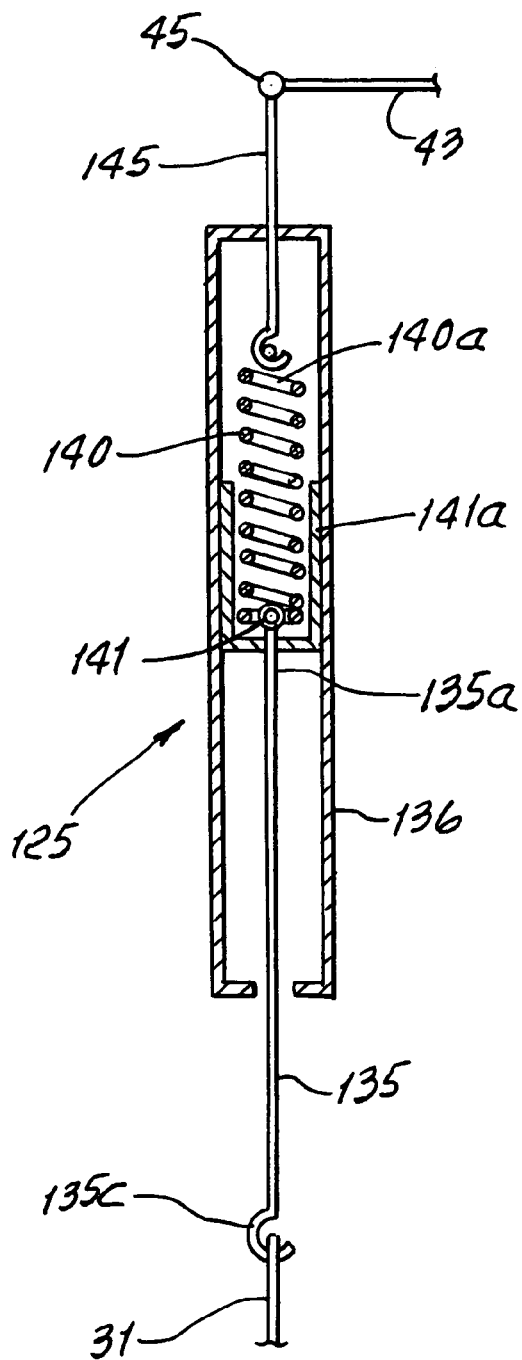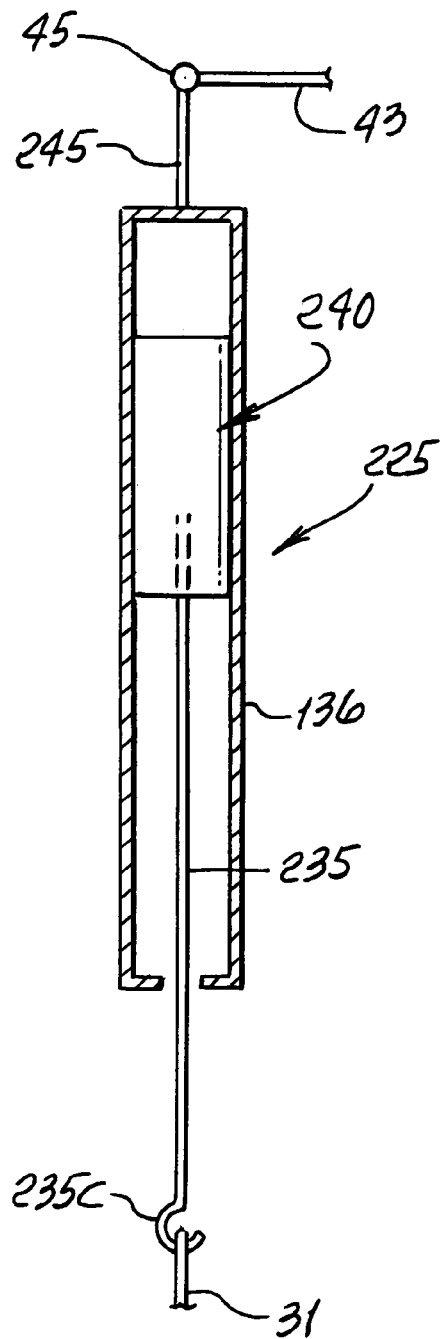

MEDICAL EXAMINATION APPARATUS

BACKGROUND OF THE INVENTION

This invention relates generally to position adjustment of surgical instrumentation, and more particularly to suspending of such instrumentation to allow movement and use thereof, in such a way as to allow increased freedom of use of the surgeon's hands, during surgery. The invention has major use in connection with accurate surgical insertion of instrumentation into the human body, as for example into the uterus for treatment or scanning thereof, and maintenance of the instrumentation in selected position, with minimum required adjustment of the instrument level.

There is clear need for apparatus and method meeting the above use requirements. No prior equipment of which I am aware meets such needs, structurally, operatively, or in terms of needed results.

SUMMARY OF THE INVENTION

It is a major object of the invention to provide apparatus and methods of use, meeting the above needs. Basically, the invention in its apparatus aspects includes:

a) a first suspension for adjustably suspending the instrumentation generally vertically, b) a second suspension operatively connected with the first suspension for adjustably suspending the instrumentation for generally horizontal movement, c) a third suspension for adjustably suspending the first and second suspensions for generally vertical movement to selected level of the instrumentation, d) and a swivel connection allowing swiveling of the instrumentation about a generally vertical axis.

A disposable connector may be provided to be connected to the first suspension for supporting the instrumentation; and the first suspension may include relatively movable rod and tube elements suspending the disposable connector, allowing accurate adjustable up-down movement of the connector and instrumentation as during surgery. The connector may be provided in such a way as to be removed after use of the instrumentation and replacing the removed used connector with a provided unused connector.

Another object is to provide the first suspension to include a spring positioned to yieldably resist adjustable movement of at least one of such elements. Compression or tension springs can be used, or a hydraulic device can be used.

A further object is to provide the second suspension to include relatively endwise telescoping components, one of the components operatively associated to the first suspension, and another of said components operatively connected to the swivel connection.

Another object is to provide for third suspension operative connection to an IV pole, whereby IV treatment is readily available in association with operation of the apparatus.

An added objective is to provide for inclusion with the third suspension of a bracket, for example intermediate the pole and the swivel connection. As a result, the apparatus, in general, has four degrees of adjustment freedom, via the first and second suspensions, the swivel and the bracket.

Additional objects include provision of suspended primary means for internally illuminating the uterus or a region thereof, and suspended secondary means for viewing the illuminated uterus or said region thereof; that secondary means including a light pipe and a camera to receive light from the light pipe.

In its basic method aspects, the invention includes:

a) providing a first suspension for adjustably suspending the instrumentation generally vertically, b) providing a second suspension for adjustably suspending the first suspension for generally horizontal movement, c) providing a third suspension for adjustably suspending the second suspension for generally vertical movement to selected level, d) providing a swivel connection allowing swiveling of the second suspension about a generally vertical axis, e) and accurately positioning said instrumentation by operating said suspensions and swivel.

The method may include provision of primary means for internally illuminating the uterus or a region thereof, and secondary means for viewing the illuminated uterus or said region thereof, and including operating the primary means.

The apparatus may then be operated to provide four degrees of adjustable movement, for accurate surgery or treatment of the body, and also freeing the surgeon's hands for attendance to desired accurate and uninterrupted surgery.

These and other objects and advantages of the invention, as well as the details of an illustrative embodiment, will be bore fully understood from the following specification and drawings, in which:

DRAWING DESCRIPTION

FIG. 2 is a plan view taken on lines 2-2 of FIG. 1;

FIG. 3 is a fragmentary elevation showing an enlarged view of a swivel;

FIG. 4 is an enlarged section taken on lines 4-4 of instrumentation shown in FIG. 1; and FIGS. 5 and 6 show modifications.

DEAILED DESCRIPTION

Figure 1:
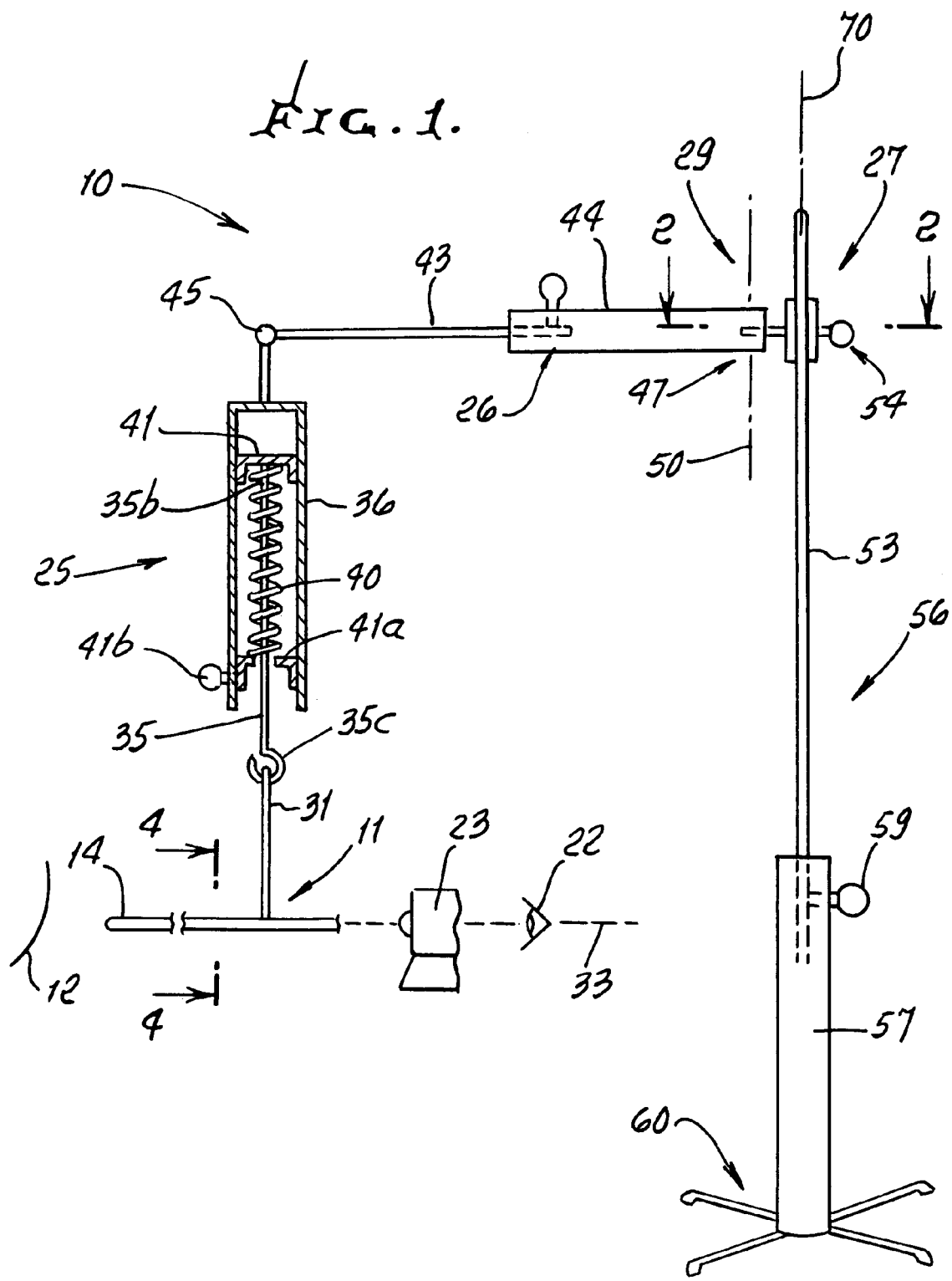
FIG. 1 is an elevation showing preferred apparatus embodying the invention.

In the drawings, showing preferred apparatus 10 (variations may of course be made), instrumentation indicated at 11 is positioned to be readily inserted endwise into a body cavity, indicated at 12, including for example the uterus. In the latter case, such instrumentation may include means for flushing the uterus, for illuminating the uterus, and for scanning same, visually or photographically or other surgery associated means. Such instrumentation may include an elongated tubular probe 14 containing a duct or multiple ducts. See for example, duct 14 to receive or supply flush water at 15 for discharge at 16 into the uterus, and duct 17 to receive flush water at 18 from the interior of the uterus, and to deliver or discharge it at 19. See also, duct 20 extending lengthwise in 13, and via which a light pipe 20a may extend to illuminate the uterus, and in which another light pipe 20b may extend for transmitting images to the user's eye 22, or to a camera, such as a video or photographic camera 23. A surgical tool 24 may also extend in 13 at 20 to sever or remove tissue, while the surgeon views the procedure.

The apparatus 10 typically includes:

a) a first suspension generally indicated at 25 for adjustably suspending the instrumentation generally vertically, b) a second suspension generally indicated at 26, operatively connected with the first suspension for adjustably suspending the instrumentation (and suspension 25) for generally horizontal movement, c) a third suspension, generally indicated at 27 for adjustably suspending the second suspension 26 (and suspension 25) for generally vertical movement to selected level of the instrumentation, for surgical or viewing procedures.

d) and a swivel connection indicated at 29 allowing swiveling of the instrumentation about a generally vertical axis, as during use.

A disposable connector 31 is operatively connected between the suspension 25 and the instrumentation 11; and that connector may advantageously comprise a flexible cord allowing forward and rearward angular manipulation of the probe 14, as during surgery, the probe being held at the general and desired selected level indicated at 33, for surgery, as by the combined suspensions, particularly 25 and 27. The surgeon's hands are therefore free for surgical purposes, without one hand being required to hold the instrumentation at desired level 33.

Suspension 25, as shown, includes relatively movable elements, such as a rod 35 and tube 36, there being a holder such as a hook 35c at the lower end of the rod to suspend cord 31. The upper end portion 35b of the rod is movable up and down in the tube, and a compression spring 40 in the tube bears upwardly against a shoulder 41 on the rod, to yieldably resist rod downward movement in the tube. As a result, the suspended instrumentation is returned to an established level, after it is raised or lowered by hand manipulation, during surgical procedure. The lower end of the spring seats at 41a, which can be upwardly or downwardly adjusted relative to tube 36, as by a set screw 41b, to adjust height 7.

Suspension 26 includes relatively endwise adjustable telescoping components 43 and 44, one component 43 operatively connected at 45 with first suspension 25, and another component 44 operatively connected to or being integral with a part 46 of a swivel connection 47, which allows swiveling of 25 and 26 about a generally vertical axis 50.

A bearing at 51 rotatably supports part 46 relative to non-rotatable part 52. The latter is connected to one member 53 of an IV pole 56, via an adjustable clamp 54. Note clamp knob 55 which, when loosened, allows adjustment sliding of the clamp, vertically, on member 53, and rotation about vertical axis 70. The latter is in turn adjustably slidable vertically in pole member 57. Members 53 and 57 are telescoping, and held in adjusted position as by a set screw 59. Accordingly, as one member 56 and/or clamp 54 is or are adjustably moved upwardly, suspensions 25 and 26 are moved upwardly, to re-set instrument nominal level 33, and vice versa. Base 60 supports the IV pole.

In summary, the three suspensions 25, 26, and 27, and the swivel 47 are supported by the IV pole; and they provide four degrees of freedom of adjustment for accurate use of the instrumentation.

The method for controlling the position of such instrumentation insertible into a body cavity, as for example the uterus, includes the steps:

a) providing a first suspension for adjustably suspending the instrumentation generally vertically, b) providing a second suspension for adjustably suspending the first suspension for generally horizontal movement, c) providing a third suspension for adjustably suspending the second suspension for generally vertical movement to selected level, d) providing a swivel connection allowing swiveling of the second suspension about a generally vertical axis, e) and positioning said instrumentation by operating said suspensions and swivel.

Four degrees of adjustment movement of the instrumentation are thereby provided.

FIG. 5 shows modified suspension 125, which includes rod 135, tube 136 and a holder such as a hook 135c at the lower end of the rod to suspend cord 31. The upper end portion 135a of the rod is movable up and down in the tube 136, and a tension spring 140 in the tube is connected at 141 to the rod upper end to yieldably resist rod downward movement to the tube. A guide 141a is slidable up and down against the tube inner wall and may be connected to the rod. The upper end 140a of the spring is suspended in the tube, as at 145, and tube 136 may also be suspended by 145.

FIG. 6 shows a further modified suspension 225, which includes a rod 235, tube 136 and a holder such as s hook 235c at the lower end of the rod, to suspend cord 31. The upper poritonof the rod is movable up and down in the tube 236, and a hydraulic device, shown schematically at 240, is connected to the end 235 yieldably resisting end downward movement in the tube as by hydraulic means in 240. Tube 136 is suspended at 245.

I claim:

1. Apparatus for effecting or controlling instrumentation insertible into the human body, as for example into the uterus, comprising in combination:
   a) a first suspension for adjustably suspending the instrumentation generally vertically,
   b) a second suspension operatively connected with the first suspension for adjustably suspending the instrumentation for generally horizontal movement,
   c) a third suspension for adjustably suspending the first and second suspensions for generally vertical movement to selected level of the instrumentation,
   d) and a swivel connection allowing swiveling of at least the first suspension about a generally vertical axis,
   e) a disposable connector connected to the first suspension for supporting said instrumentation,
   f) first suspension including relatively movable rod and tube elements suspending the disposable connector, allowing accurate adjustable up-down movement of the connector and instrumentation as during surgery,
   g) a support means positioned to yieldably resist adjustable movement of at least one of said elements,
   h) said support means including one of the following:
      i) a tension spring,
      ii) a compression spring,
      iii) a hydraulic device.

2. The combination of claim 1 wherein said second suspension includes relatively endwise telescoping components, one of said components operatively associated with the first suspension, and another of said components operatively connected to said swivel connection.

3. The combination of claim 2 wherein said components are generally horizontally relatively movable.

4. The combination of claim 1 wherein said third suspension has operative connection to an IV pole.

5. The combination of claim 4 wherein said third suspension includes a bracket adjustably connected to said IV pole, whereby the bracket and swivel are adjustably positioned, vertically.

6. The combination of claim 5 wherein said apparatus has four degrees of adjustment freedom, via said first and second suspensions, said swivel and said bracket.

7. The combination of claim 1 including an IV pole, via which said first, second, and third suspensions and swivel are supported.

8. The combination of claim 7 wherein said first, second, and third suspensions and said swivel provide four degrees of adjustment freedom for said instrumentation.

9. The combination of claim 1 including said instrumentation, which includes means for flushing the uterus.

10. The combination of claim 1 including said instrumentation which includes primary means for internally illuminating the uterus or a region thereof, and secondary means for viewing the illuminated uterus or said region thereof.

11. The combination of claim 10 wherein said secondary means includes a light pipe, and a camera to receive light from the light pipe.

12. The method for controlling the position of instrumentation insertible into the human body as for example into the uterus, that includes the steps:
   a) providing a first suspension for adjustably suspending the instrumentation generally vertically,
   b) providing a second suspension for adjustably suspending the first suspension for generally horizontal movement,
   c) providing a third suspension for adjustably suspending the second suspension for generally vertical movement to selected level,
   d) providing a swivel connection allowing swiveling of the second suspension about a generally vertical axis,
   e) and positioning said instrumentation by operating said suspensions and swivel,
   f) there being a disposable connector connected to the first suspension for supporting said instrumentation,
   g) and wherein the first suspension is provided to include relatively movable rod and tube elements suspending the disposable connector, allowing accurate adjustable up-down movement of the connector and instrumentation as during surgery,
   h) there being support means positioned to yieldably resist adjustable movement of at least one of said elements,
   i) said support means including one of the following:
      i) a tension spring,
      ii) a compression spring,
      iii) a hydraulic device.

13. The method of claim 12 wherein said step e) includes adjusting the relative positions of said elements.

14. The method of claim 12 including removing said disposable connector after use of said instrumentation and replacing said removed used connector with a provided unused connector.

15. The method of claim 12 wherein said instrumentation includes primary means for internally illuminating the uterus or a region thereof, and secondary means for viewing the illuminated uterus or said region thereof and including operating said primary means.

16. The method of claim 12 including providing an IV pole to which said third suspension has operative connection.

* * * * *